United States Patent
Sines et al.

[11] Patent Number: 5,860,434
[45] Date of Patent: Jan. 19, 1999

[54] DENTAL FLOSSING DEVICES

[75] Inventors: Randy D. Sines; David A. Krise, both of Spokane, Wash.

[73] Assignee: Digideal, Spokane, Wash.

[21] Appl. No.: 827,282

[22] Filed: Mar. 28, 1997

Related U.S. Application Data

[63] Continuation-in-part of Ser. No. 626,774, Apr. 2, 1996, abandoned.

[51] Int. Cl.[6] .................................................... A61C 15/00
[52] U.S. Cl. ......................... 132/323; 132/329; 132/325
[58] Field of Search .................................. 132/323, 324, 132/325, 326, 327, 329, 200; 433/141, 142, 143

[56] References Cited

U.S. PATENT DOCUMENTS

| | | | |
|---|---|---|---|
| 691,581 | 1/1902 | Baumeister | 132/323 |
| 1,260,011 | 3/1918 | Muchow . | |
| 1,498,853 | 6/1924 | Oliver . | |
| 1,534,171 | 4/1925 | Fickes . | |
| 1,771,026 | 7/1930 | Bohm | 132/326 |
| 2,187,899 | 1/1940 | Henne | 132/323 |
| 2,354,454 | 7/1944 | Geffner | 132/323 |
| 2,443,415 | 6/1948 | Buscarino | 132/323 |
| 2,451,849 | 10/1948 | Massimiano . | |
| 2,612,176 | 9/1952 | Sam | 132/323 |
| 2,754,833 | 7/1956 | Vecchio . | |
| 3,848,613 | 11/1974 | Sheehan . | |
| 4,013,085 | 3/1977 | Wright . | |
| 4,460,002 | 7/1984 | Burdette, Jr. . | |
| 4,531,530 | 7/1985 | Aiken . | |
| 4,597,398 | 7/1986 | Chu | 132/323 |
| 4,727,895 | 3/1988 | Berarducci | 132/323 |
| 4,807,651 | 2/1989 | Naydich . | |
| 5,050,625 | 9/1991 | Siekmann . | |
| 5,101,843 | 4/1992 | Peng . | |
| 5,139,038 | 8/1992 | El Gazayerli . | |
| 5,184,631 | 2/1993 | Ikeda | 132/323 |
| 5,280,797 | 1/1994 | Fry . | |
| 5,482,466 | 1/1996 | Haynes . | |
| 5,538,023 | 7/1996 | Oczkowski et al. . | |

FOREIGN PATENT DOCUMENTS

| | | | |
|---|---|---|---|
| 4310432 | 1/1994 | Germany | 132/323 |

*Primary Examiner*—Gene Mancene
*Assistant Examiner*—Pedro Philogene
*Attorney, Agent, or Firm*—Wells, St.John, Roberts, Gregory & Matkin, P.S.

[57] ABSTRACT

Dental flossing devices and methods which are of particular use with corrective dental braces. The flossing devices utilize a strand of floss supported by an arm attached to a grip. The arm includes one or more extensions which support the floss and can be inserted under a brace wire. An extension which is more flexible and curved facilitates tensioning of the floss when forced against a tooth. In another embodiment a supply roll of floss is included. Other flossing devices include a loop which is engaged by the user's finger.

11 Claims, 8 Drawing Sheets

DENTAL FLOSSING DEVICES

CROSS-REFERENCES TO RELATED CASES

This is a continuation-in-part application based upon U.S. patent application Ser. No. 08/626,774, filed Apr. 2, 1996, now abandoned.

TECHNICAL FIELD

This invention concerns dental flossing devices and methods for supporting a length of floss and enabling an individual to floss between adjacent teeth. The devices and methods are of particular advantage to those who wear dental braces.

BACKGROUND OF THE INVENTION

Individuals with dental braces frequently encounter difficulty when attempting to floss their teeth. This difficulty stems from the fact that the braces pose an obstacle to a strand of floss being inserted between the teeth as desired to clean along the gum line. Dental braces usually include anchoring mechanisms which are centered and glued onto the distal faces of the teeth. A wire extends across the distal faces supported by the anchoring mechanisms and spans adjacent teeth. The spanning wire is usually located about midway between the gum line and the top or bottom cutting edges of the teeth. The spanning brace wire presents a formidable challenge for an individual wishing to floss between adjacent teeth near the gum line. This occurs because the floss may only be inserted so far as the spanning brace wire. The remaining space between the gum line and the spanning wire typically goes unflossed because the individual finds it difficult or impossible to insert a piece of dental floss into the small space between adjacent teeth, the gum line and the spanning brace wire.

People who do not have dental braces also frequently experience difficulty in adequately supporting a strand of dental floss. Conventional dental floss is most typically supported by spooling the ends of the strand of dental floss about the index fingers. The exposed segment of the strand is then positioned between the teeth and manipulated to dislodge materials from the teeth and gum line. This technique is disadvantageous for many people who do not have strong hands and fingers, such as many children and older people. Even for others who can adequately support the segment of dental floss, the experience can be less than optimal.

The present invention was developed to provide improved flossing and improved convenience in performing flossing, particularly for individuals with dental braces.

BRIEF DESCRIPTION OF THE DRAWINGS

Preferred embodiments of the invention are described below with reference to the following accompanying drawings.

FIG. 4 is a perspective view of a third form of dental flossing device including aspects of the invention. A portion is broken away to show a supply of floss.

FIG. 5 also shows movement of the flossing device into different positions in phantom lines.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

First Embodiment

Figure 1:
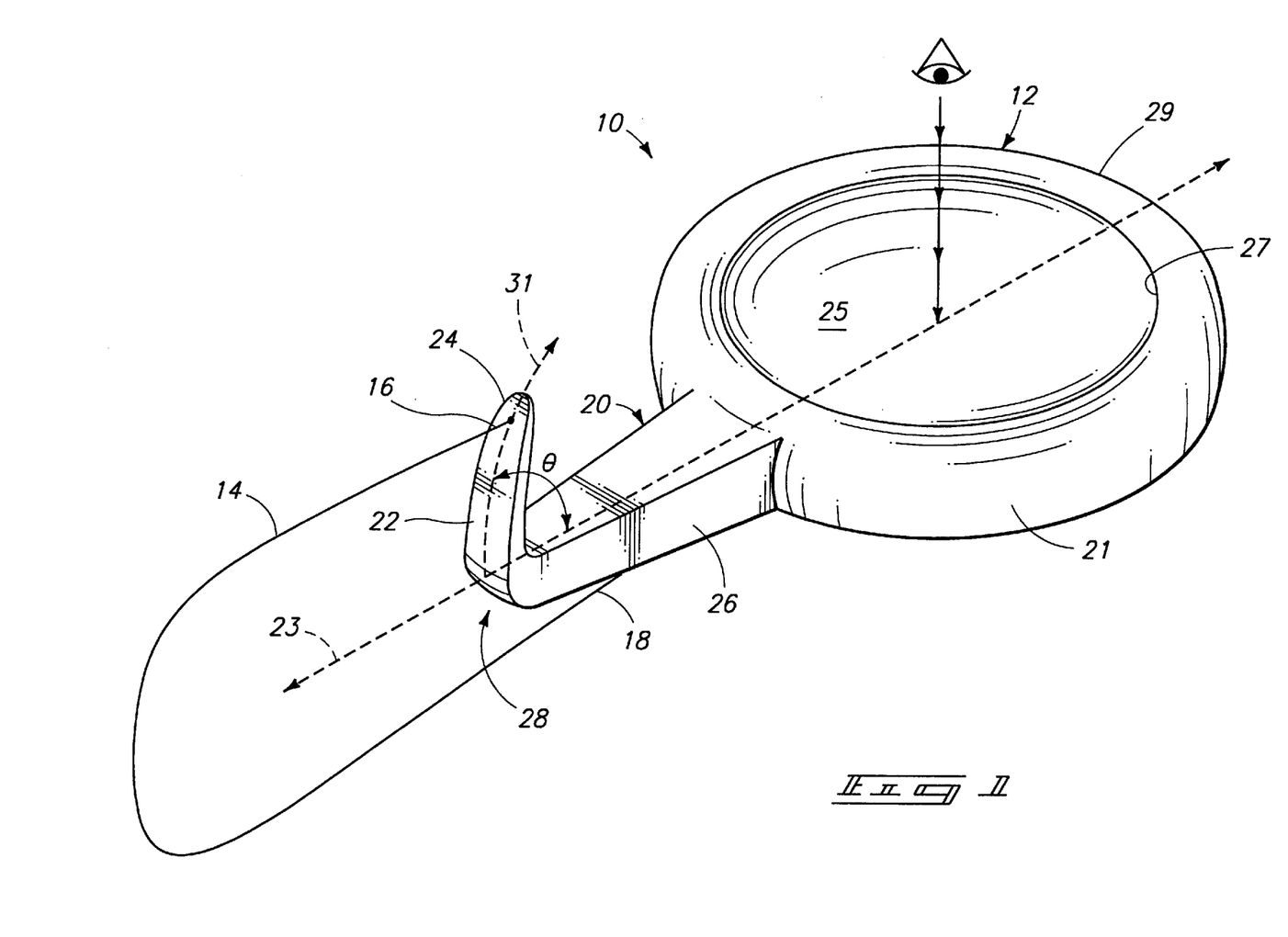
FIG. 1 is a perspective view of a first preferred embodiment of dental floss support device including aspects of this invention.

FIG. 1 shows a first preferred embodiment of dental flossing device 10 made in accordance with aspects of the present invention. Device 10 includes a grip 12 which is suitably shaped and used by a user to grip the device. Grip 12 can be of various shapes. As shown, grip 12 has an approximately circular periphery 21. The generally circular shape is seen when viewed in plan from a point transverse to main arm axis 23 (shown graphically in FIG. 1 by the multi-headed arrow).

Grip 12 also advantageously includes a dished central region 25 which is designed to receive a portion of a user's finger (not shown in FIG. 1). The marginal portions adjacent to the peripheral edge of the grip are relatively thicker for added strength and to allow the central region to be contoured into the dished upper surface configuration. An optional non-slip grip pad 27 can be provided for facilitating gripping by an individual. Grip pad 27 may be any suitably textured surface which promotes secure gripping by the user. Alternatively, the grip can be provided with a texturized surface in lieu of pad 27. Grip 12 also includes a grip end 29 which is diametrically spaced from the opposing arm 20.

Figure 2:
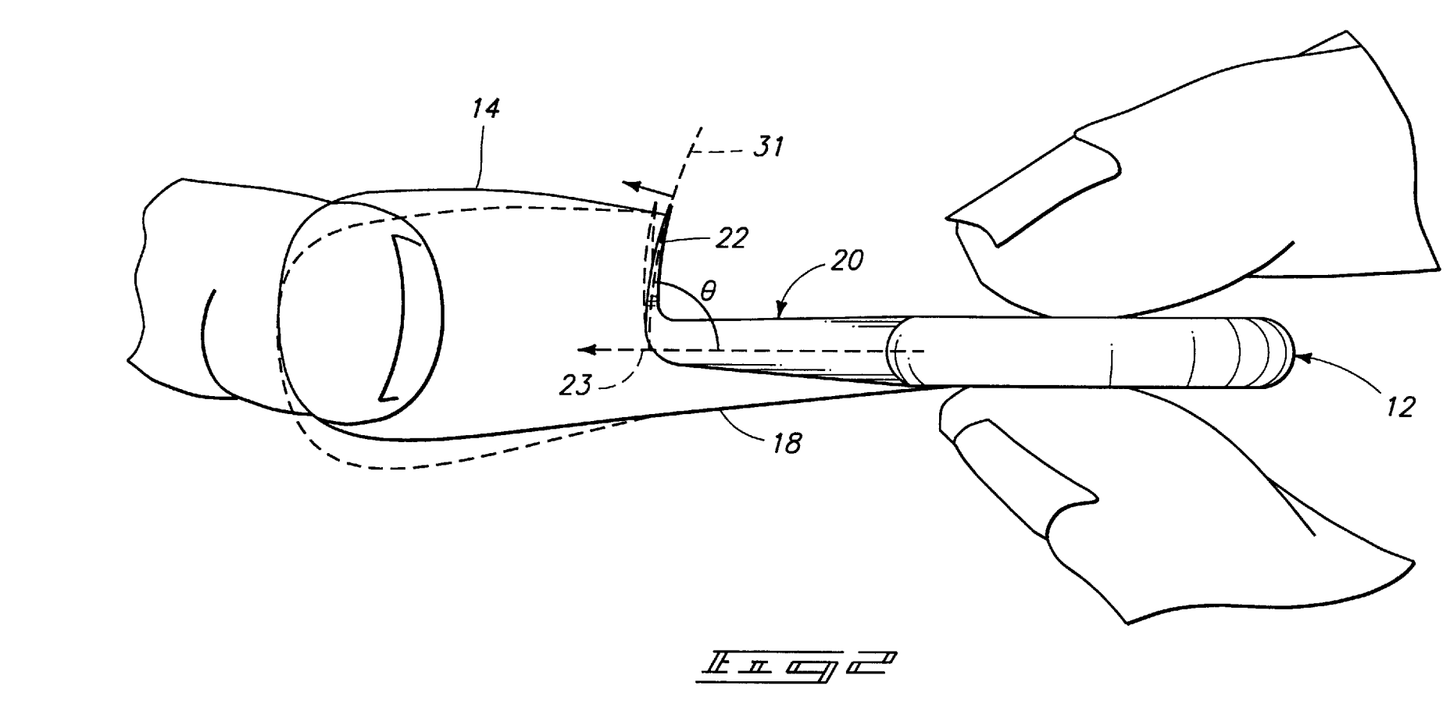
FIG. 2 is a side elevational view of the device of FIG. 1, showing the device being gripped between a thumb and forefinger of an individual's right hand, and showing the preferred loop of floss being engaged by the index finger of the individual's left hand for applying tension to the floss.

Flossing device 10 includes arm 20 which is connected to grip 12. Arm 20 is preferably elongated and extends outwardly from grip 12. FIGS. 1 and 2 show that arm 20 is advantageously cantilevered relative to grip 12. The arm 20 includes a main arm portion 26 which extends and defines a main arm axis 23. In the embodiment of FIG. 1, the main arm is formed so that the associated main arm axis 23 is approximately straight. The main arm is also preferably constructed with the axis angled slightly upwardly relative to a basal surface formed by the lower portions of grip 12. As shown, arm 20 also is tapered outwardly from grip 12. This removes the arm from a supporting surface when the flossing device is situated on a counter or other surface. This construction aids in maintaining the arm in reduced risk of being exposed to bacteria or other contaminants which may be present upon the counter or other surface.

Arm 20 also includes an extension portion 22 which is connected to the main arm 26. The extension 22 has a distal end 24. A connection between extension 22 and main arm 26 can advantageously be provided by a dog-leg or hooked bend 28. As shown, main arm part 26 is advantageously tapered in dimension along axis 23 as the arm proceeds from its connection point adjacent grip 12 toward the connecting bend 28.

The arm includes a floss support feature which is preferably formed upon extension 22 for supporting portions of a length or strand of floss 14. The preferred floss support feature is described in greater detail below. The strand of floss 14 has opposing ends 16 and 18. The ends of the strand of floss are connected to the device in a suitable fashion, such as explained more fully below.

In the embodiment of FIG. 1, the strand of floss 14 is connected in a manner which forms a finger-engageable loop. The loop extends from the floss-supporting extension to allow an individual to engage the loop with a finger to tension the length of floss relative to the floss support feature or distal end 24 as shown best in FIG. 2. The opposing end 18 of the dental floss is captured and held between the grip 12 and thumb, as shown in FIG. 2. Alternatively, it can be molded, adhered, or otherwise affixed to the grip.

Floss-supporting extension or extension arm part 22 extends along a floss-supporting extension part axis 31 which extends angularly away from main axis 23. Preferably, bend 28 is of a magnitude such that floss-supporting extension axis 31 forms an angle θ with main axis 23 in the range of between 45° to 135°, more preferably 60° to 120°; even more preferably, angle θ is in the range of approximately 75° to 105°, and still more preferably around 90°.

As shown, floss-supporting extension 22 is generally tapered in dimension along axis 31 from bend 28 toward distal end 24. The tapered shape of floss-supporting extension 22 is preferably to facilitate use with dental braces and to provide a resilient flexing action, as best shown in FIG. 2. The tapered shape also allows the extension to be used as a toothpick. The flexing action occurs in a direction generally transverse the floss-supporting extension axis 31 in response to forces applied through loop 14 as the loop is tensioned relative to the grip. More specifically, a finger is shown at the left-most side of FIG. 2 engaging floss loop 14 and moving the loop to a position shown in phantom lines. As a result, floss-supporting extension 22 is moved to a position shown in phantom lines. This flexibility promotes a longitudinal reciprocating action of the floss within the space between adjacent teeth, thereby enhancing an individual's ability to clean their teeth along the gum line.

The floss support feature mentioned above supports floss end 16 on floss-supporting extension 22 adjacent distal end 24. Preferably, the IS floss support feature includes an aperture (not specifically designated) through which a region of floss end 16 is positioned and secured or tied off in an appropriate manner, such as a knot. This permits floss end 16 to be positioned closely adjacent an individual's gum line when floss-supporting extension 22 is inserted under a brace wire described in more detail below. The floss support feature also supports floss end 18 on any convenience location on device 10 so that floss length 14 may be formed into a finger-engageable loop for allowing an individual to engage the loop with a finger and thereafter tension the length for flossing. It should also be appreciated that floss end 18 may not be connected on device 10 at all, but rather may be left free relative to device 10. In this case, an individual would grasp the floss against grip 12, or alternatively, wind floss end 18 around a finger to supply the desired restraint and application of tension.

Second Embodiment

Figure 3:
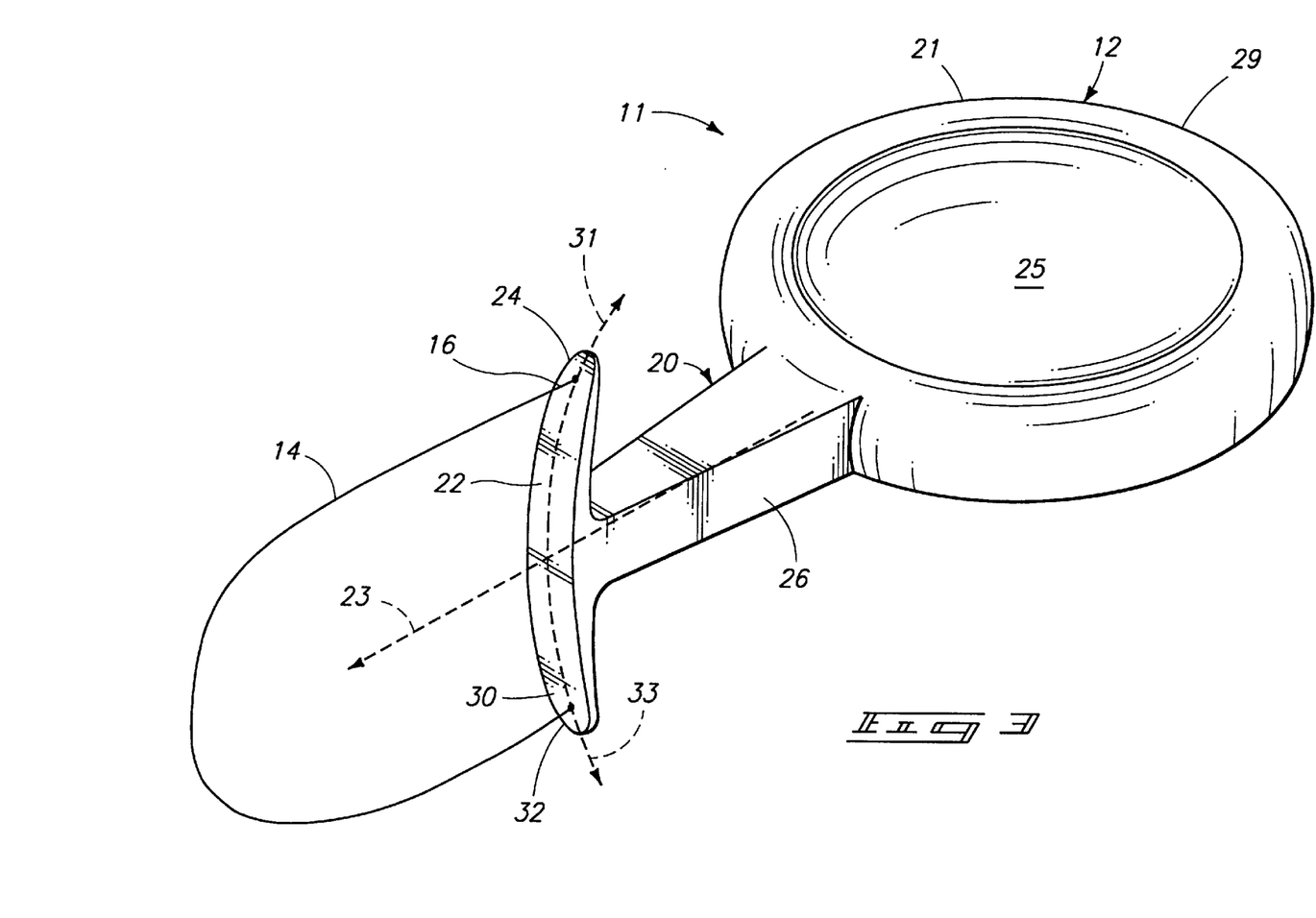
FIG. 3 is a perspective view of a second form of dental flossing device including aspects of the invention.

FIG. 3 shows an alternate embodiment flossing device 11 of the present invention wherein like elements have been identified with similar reference numbers. The reader will notice a second floss-supporting extension or extension arm part, identified by numeral 30. Second extension arm part 30 is joined to main arm part 26 and extends angularly away therefrom along a second extension arm part axis 33 toward a distal end 32. Preferably, the extension arm parts 22, 30 extend away from main axis 23 and in directions generally opposite one another along such axes. The opposing relationship can be colinearly opposite or at displaced positions along the main arm 26. The directly opposing construction shown gives the device, and particularly arm 26 and floss-supporting extensions 22, 30 a hammer head-like appearance. As in the embodiment of FIG. 1, each respective extension arm part axis 31, 33 forms an angle with main axis 23 which is in the range of between 45° to 135°, more preferably 60° to 120°, even more preferably 75° to 105°, still more preferably around 90°.

The floss support feature in this embodiment supports respective floss ends 16, 18 adjacent respective distal ends of each floss-supporting extension. The floss support feature is provided in the form of two apertures, one each in a respective distal end which allows a corresponding portion of the floss end to be inserted therethrough and tied off or otherwise secured in an appropriate manner. It should be understood that the above-described apertures in the respective distal ends of the floss-supporting extensions are preferred only, and are not intended to exclude other means and ways of supporting a length of floss. Similar to the embodiment of FIG. 1, each of the respective extension arm parts 22, 30 is flexible in a direction generally transverse to the respective arm part axes 31 and 33, such as in response to finger-developed tension on the floss loop. This is advantageous for promoting the reciprocal floss motion mentioned above.

Third Embodiment

FIG. 4 shows another flossing device 34 constructed according to some of the aspects of the present invention. Device 34 is a dental flossing apparatus which both supports and supplies new strands of dental floss. The apparatus enables an individual with braces to not only floss between adjacent teeth, but to also dispense floss from a supply which is held on the apparatus.

Flossing apparatus 34 includes a frame 36 having an elongate arm 38 with a distal end 40. The distal end has a cross-sectional profile which is thinly dimensioned and sufficiently slender so as to allow the extension to be inserted between a brace wire and adjacent teeth (similar to FIG. 5). This allows the distal end of the arm and attached dental floss to come into close proximity with an individual's gum line adjacent the teeth.

Apparatus 34 includes a supply of floss 42 which is advantageously provided on frame 36 for supplying a length of floss which is trainable along desired areas of frame 36 and arm 38. A floss support feature on the arm supports a length of floss 44 in a manner allowing a finger-engageable loop to be formed and engaged by an individual's finger to tension the length of floss for use. Engagement of the user's finger along the inside of the teeth is shown in FIG. 4 with respect to the first-described embodiment.

As shown in FIG. 4, frame 36 includes an enclosure 46, a portion of which has been broken away to show floss supply 42. The enclosure holds the floss supply, which preferably includes a spool 48 about which a desired amount of floss may be wound for selectively supplying an individual with new floss. Enclosure 46 may be selectively opened for installing a new supply of floss once the previous supply is exhausted. In the embodiment shown the enclosure cover 47 is detachable by a snap fit with other parts of the frame 36 to allow replacement or adjustment of the floss supply spool and attached floss. Alternatively, device 34 may be disposable so that once the spool or other supply of floss is fully exhausted, the device is thrown away. It should be understood, however, that the preferred supply in the form of a spool configuration is not intended to exclude other means for supplying or holding a supply of floss.

Adjacent the supply of floss, and to the left as shown in FIG. 4, a floss exposure area 50 is provided in the form of an opened, rectangular and recessed area which exposes a length of trained floss for promoting digital or finger capture against the frame. This prevents the floss from spooling out from the supply when an individual applies finger tension to the floss loop 44 for flossing their teeth. Exposure area 50 includes a secondary recess 52 over which the trained floss passes for facilitating grasping of the floss between an individual's thumb and forefinger, and for advancing new floss from the supply of floss after the floss loop has been used for flossing the teeth.

FIG. 4 shows that arm 38 includes a main arm part 54 which extends along a generally straight main arm part axis 55, and an extension arm part 56 joined to main arm part 54. Extension arm part 56 extends along an extension arm part axis 57 toward distal end 40. Preferably, arm 38 includes a bend 58 between main arm part 54 and extension arm part 56 and the bend defines an angle θ between the extension arm part axis 57 and the main arm part axis 55. Angle θ is preferably as described above in connection with the other embodiments of the invention.

As shown in FIG. 4, the floss is trained along frame 36, through floss exposure area 50, over recess 52, and extends downwardly into a hollow passage within the interior of main arm part 54. The floss emerges from the hollow passageway through a floss emission aperture 60 and extends upwardly toward the distal end 40 of the arm 56. A first floss loop support feature in advantageously provided in the form of a distal aperture 62 formed through arm 56 adjacent distal end 40. The aperture 62 forms a support passage through which the floss passes in order to support the floss adjacent to the floss loop 44.

The flossing apparatus 34 also includes a second floss loop support feature which is advantageously provided in the form of a tie-off nib or capstan 64 attached at a suitable point to the apparatus. As shown, the tie-off nib 64 is provided on the arm 38 at a position on the main arm part 54 adjacent bend 58 and in opposing relationship to extension part 56. Alternative second floss loop support features may be constructed in various configurations and positioned at a variety of convenient locations.

To form a floss loop, an individual need only insert a floss end through aperture 62, pull a desired amount of floss through the aperture, and wrap the floss around nib 64. This also enables an individual to adjust the dimension of the loop as they find most desirable.

The flossing apparatus 34 further preferably includes a floss cutoff in the form of cutoff blade 66. The cutoff is provided on the apparatus at a suitable location, such as along the underside of the frame, rearwardly of nib 64. The cutoff allows a user to cut off floss which has been used as loop 44 in a prior session. Cutoff 66 can also be used to dispose of unneeded surplus floss.

It will be appreciated that the floss loop 44 may be supported on the arm by the floss support features in a variety of suitable manners which enables an individual to form a desired floss loop. For example, the floss may be trained from the bottom of the extension arm part 56 and tied off adjacent distal end 40. Alternatively, the end of the length of the floss wrapped around nib 64 may freely dangle for enabling an individual to simply wrap the floss around a finger for applying the desired tension and flossing.

Fourth Embodiment

Figure 6:
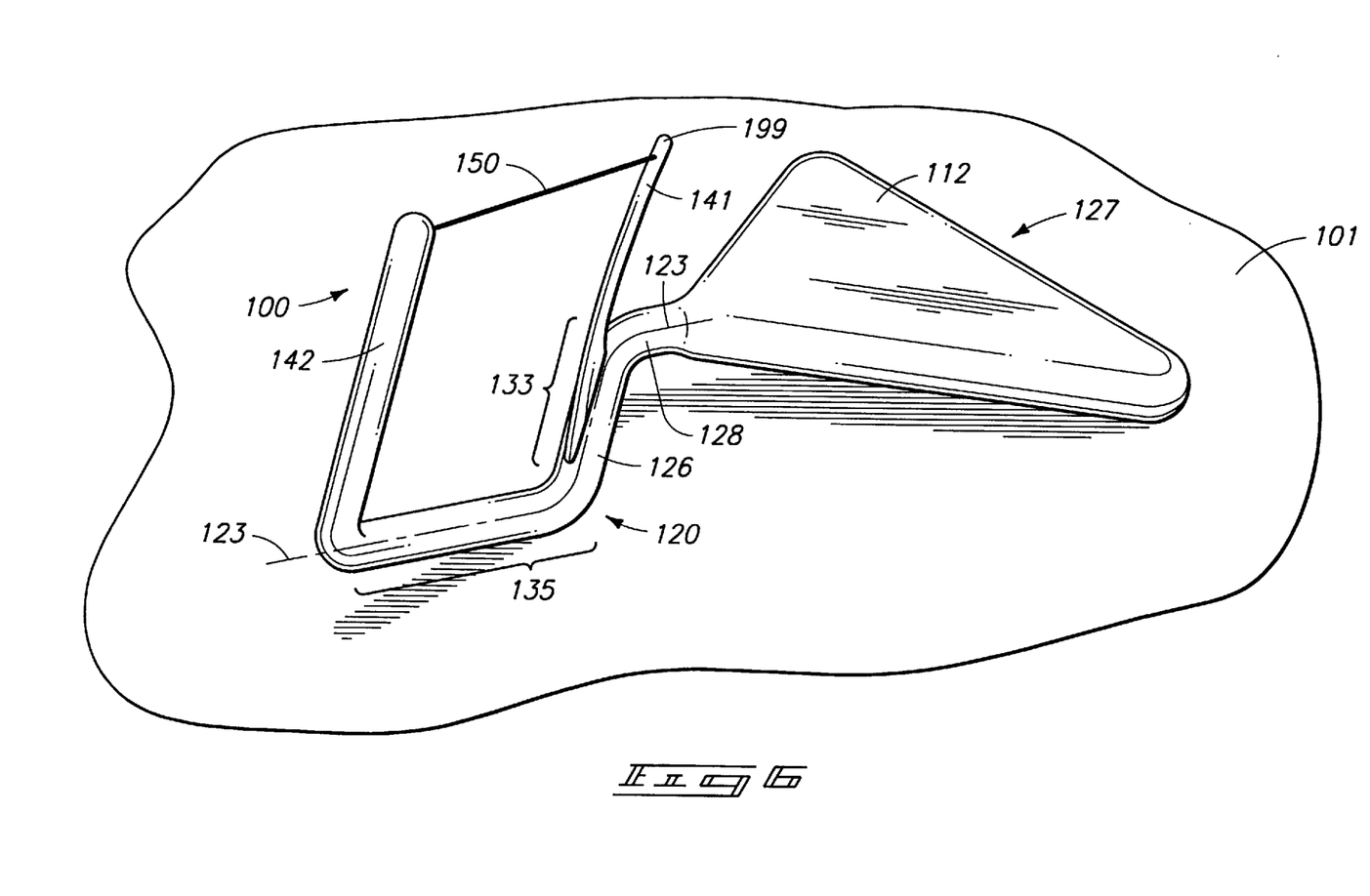
FIG. 6 is a perspective view of a fourth form of dental flossing device made according to the invention.
Figure 7:
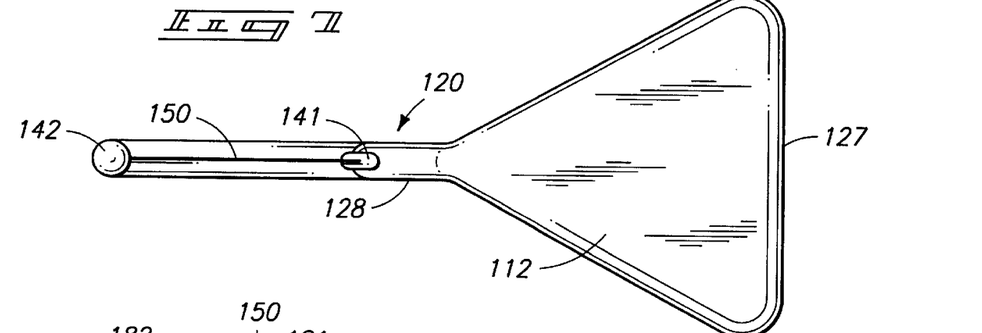
FIG. 7 is a top view of the flossing device of FIG. 6.

FIGS. 6–12 show a fourth embodiment 100 according to aspects of the current invention. FIG. 6 shows dental flossing device 100 in perspective and resting upon a supporting surface 101. Flossing device 100 includes a grip 112 which is advantageously formed as a planar member. The planar member can be in different shapes although a preferred shape is the triangular shape shown. The triangular shape is preferably connected to the arm 120 in such a manner that the arm connects at an apex 123 of the triangular grip and there is an opposing base 127 of the triangle.

The arm member 120 includes a main arm or main arm part 126 which is connected to the grip 112 at a neck portion 128. The main arm includes neck portion 128 and an offset portion 133. The offset portion 133 is joined to a transdental portion 135 which spans across a space adjacent to a user's teeth during use. The portions 128, 133 and 135 each have associated axis portions which together form a composite main arm axis 123.

As FIG. 6 illustrates, lower portions of offset 133 and the base 127 of grip 112 act together to form a supporting rest which positions the device 100 in an upright position upon the supporting surface. In this upright position the grip 112 is largely spaced from the supporting surface, as is all of the main arm 126 except for the contacting heel along the bottom of the juncture between the offset portion 133 and the transdental portion 135. As shown in the preferred construction, the rest is defined by the base 127 along a contact line formed thereby, and by the contact point at the contact heel. This effectively forms a rest which functions similar to a tripod, or small protrusions can be added at the outer corners of base 127 to form a tripod.

FIGS. 6–12 also show that the arm 120 includes a first arm extension 141 and a second arm extension 142. First extension 141 is adjacent to the grip 112, and second arm extension 142 is advantageously outward relative to the first extension. The extensions 141 and 142 are preferably oriented within the angular ranges as described hereinabove relative to the main arm axis 123 along the transdental segment 135.

One of the extensions 141 or 142 is preferably made relatively more flexible in bending as compared to the other of said extensions to allow a user to tension the strand of dental floss 150 which extends across between the extensions. As shown, the more flexible extension is first extension 141 which is proximate or adjacent to grip 112. This construction allows the user to bend the more flexible extension by forcing it against a user's teeth as shown by applying a suitable force, such as in the approximate direction of force arrow 153 shown in FIG. 12. The relatively greater degree of flexibility in bending of first extension 141 versus the relatively more rigid structure provided by second extension 142 facilitates application of moderate amounts of force while still allowing easy tensioning of the floss strand 150.

Figure 8:
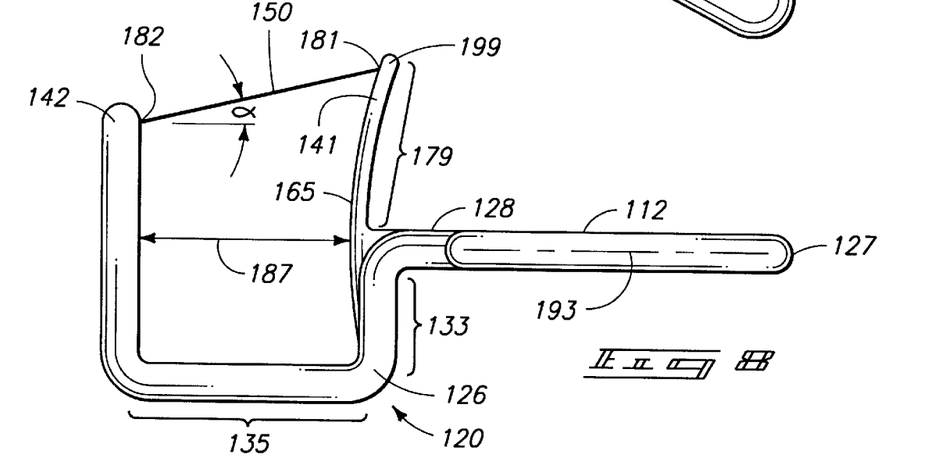
FIG. 8 is a side elevational view of the flossing device of FIG. 6, the opposite side being a mirror image of FIG. 8.
Figure 9:
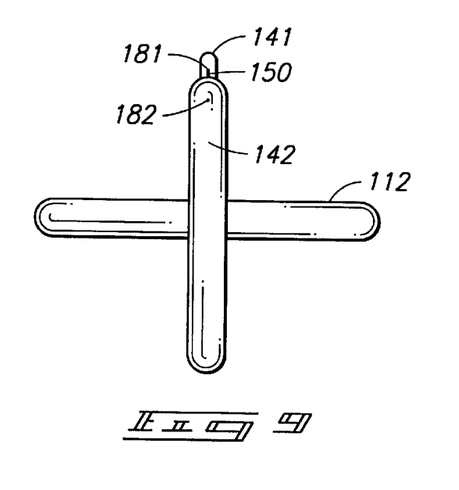
FIG. 9 is a left end view of the flossing device of FIG. 6.
Figure 10:
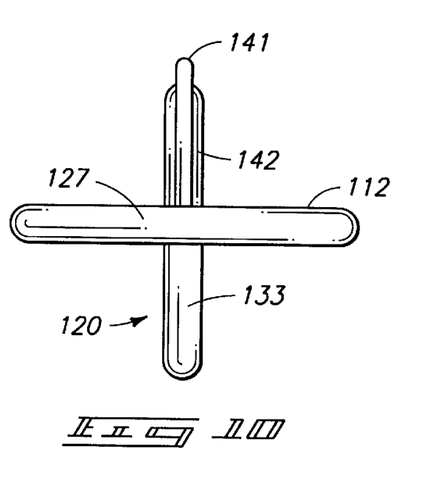
FIG. 10 is a right end view of the flossing device of FIG. 6.
Figure 11:
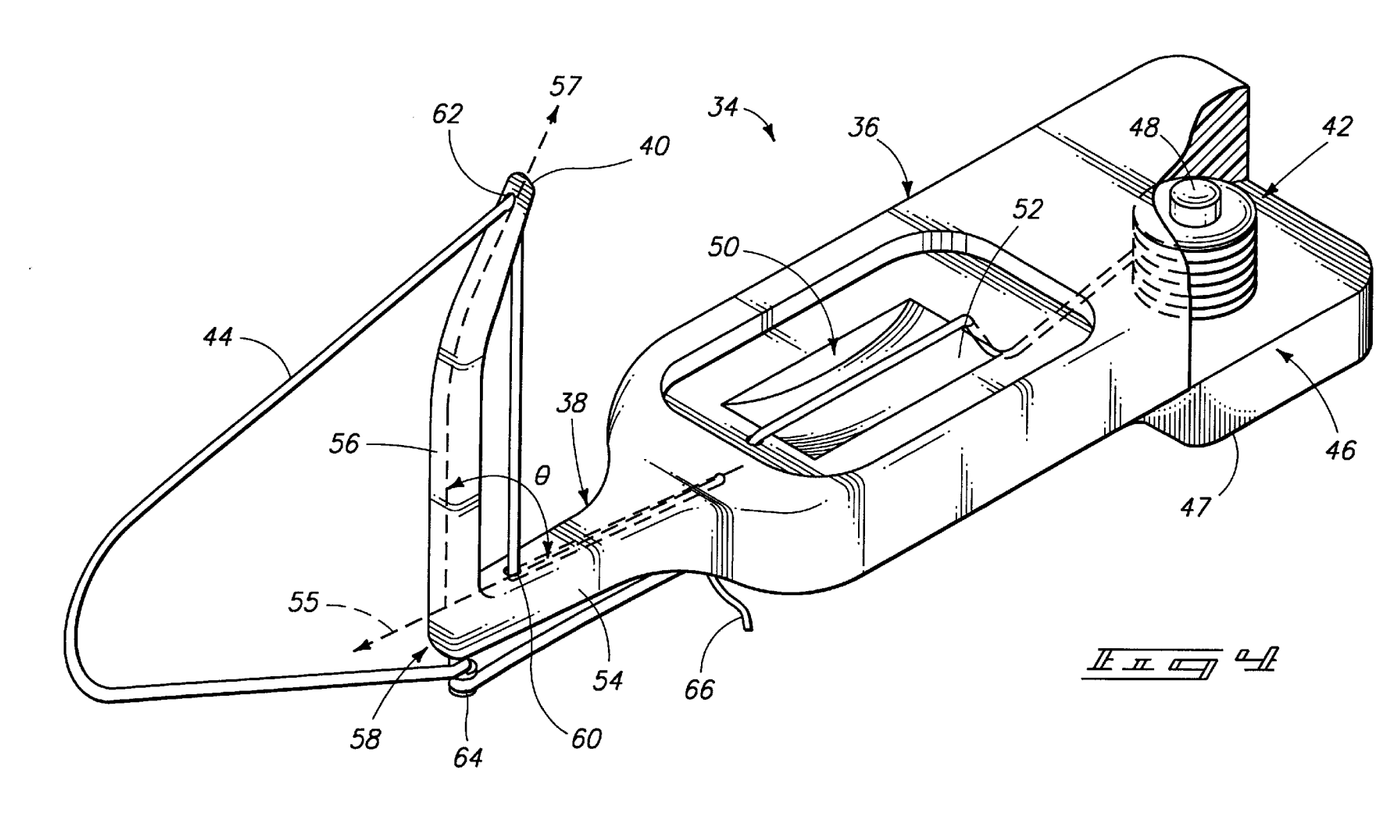
FIG. 11 is a bottom view of the flossing device of FIG. 6.
Figure 12:
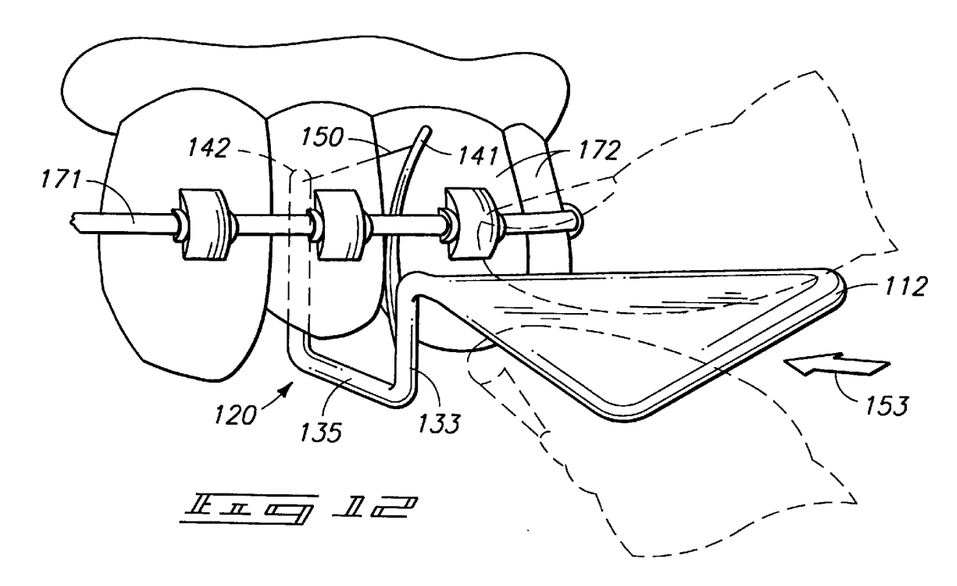
FIG. 12 is a perspective view showing the flossing device of FIG. 6 in operation within a user's mouth.

FIG. 8 illustrates that arm 120 is preferably provided with at least one extension which has a curved shape. As shown, the curved inward face 165 is formed as part of the first extension 141. The curved face is adjacent to the transdental space between extensions 141 and 142. FIG. 12 indicates that the curved inward face allows a user to press the curved face against a tooth or teeth of the user to perform the tensioning effect described above. The curved inward face also allows a user to easily rock the flossing device in a rocking motion which facilitates moving the strand of floss 150 within the intersticial space relative to teeth and gums to dislodge materials therefrom. The slender curved extension 141 can also be used as a toothpick.

The slender nature of first extension 141 allows it to be inserted between a dental brace wire 171 and adjacent surfaces of teeth 172. This is typically done along the intersticial space between adjacent teeth. The slender portions of extensions 141 act as an insertable part of the extension. The curved nature of extension 141 also aids in use of the device 100 since it helps to retain the device in the installed position shown in FIG. 12 due to the fact that the distal end of extension 141 is hooked back over a portion of the brace wire 171 thus inhibiting displacement of the device from the installed operative position.

The distal ends of extensions 141 and 142 are advantageously provided with at least one floss support feature 181 and 182 (FIG. 8) which are in the preferred embodiment illustrated provided in the form of apertures which receive the strand of floss. The strand of floss is advantageously molded in-place within apertures 181 and 182 to improve bonding and mechanical strength of the support features. Alternative means for supporting the strand of floss are alternatively possible.

FIG. 8 shows that the floss support features 181 and 182 are advantageously positioned upon the first and second extensions 141 and 142 so as to place the floss at a floss incline angle α. Angle α is with respect to a reference line which is parallel to a longitudinal grip axis or plane 193. The floss incline angle is preferably in the range of approximately 5°–25° of arc. The inclination is preferably oriented so that the second extension floss support 182 is closer to the grip axis 193 than is the first extension support 181. This inclination angle of the floss facilitates positioning the strand of floss 150 within an intersticial crevice between adjacent teeth.

The first extension also preferably includes a distal tip end 199 which is the portion of extension 141 which is distal relative to support feature 181. The distal tip end is provided to facilitate the easy insertion of the first extension between a brace wire and teeth of the user. The distal tip end is preferably used by moving the flossing device toward the teeth, such as aligned upon an intersticial crevice between teeth. The tip end 199 engages with the outward surfaces of the teeth. The user then inserts the first extension between the brace wire and teeth with the floss strand 150 moving into the intersticial crevice. Without the overhanging tip end 199 the user will find it difficult to properly place the first extension against the teeth.

Exemplary Sizes

Turning now to a discussion of some preferred dimensional aspects of the embodiments of FIGS. 1 and 2, a suitable diameter for grip 12 has been found to be less than around one and one half inches (~37 millimeters). A suitable length from diametrically-spaced grip end 29 to the bend in the arm is less than about two inches (~51 millimeters), and the length from the bend in the arm to a respective floss-supporting distal end is less than about one half inch (~12 millimeters).

With respect to the embodiment of FIG. 4, the dimensions are similar to those discussed above relating the embodiments of FIGS. 1 and 2. It is to be understood that the above-described dimensional aspects are preferred only, and are not intended to unnecessarily limit the invention. As such, dental floss support devices with dimensional aspects other than those preferred aspects mentioned above are considered within the spirit and scope of the invention.

With regard to the embodiment of FIGS. 6–12, the overall length of the flossing device 100 is advantageously about 1.5–2 inches (~38–51 millimeters), more preferably 1.7 inch (43 millimeters). About 0.8–1.2 inch (~20–30 millimeters), more preferably 1 inch (~25 millimeters) is devoted to the length of grip 112 and the remainder is associated with the arm portion 120, including the main arm 126 and extensions 141 and 142. The first extension is approximately 0.4–0.6 inches (~10–15 millimeters) long and about 1 millimeter in diameter along the insertable portion 179. The second extension is approximately 0.5–0.7 inches (~12–17 millimeters) long and approximately 2–3 millimeters in diameter. The offset portion 133 of the main arm is advantageously about 0.2–0.4 inch (~5–10 millimeters). The transdental gap 187 is approximately 0.4–0.6 inch (~10–15 millimeters). The distal tip end 199 is approximately 1–4 millimeters in length distal from the floss support feature 181.

It should be appreciated that the sizes given above may vary. In particular, diametral sizes may vary dependent upon the material being used to produce all or parts of the device.

Methods and Operation

Figure 5:
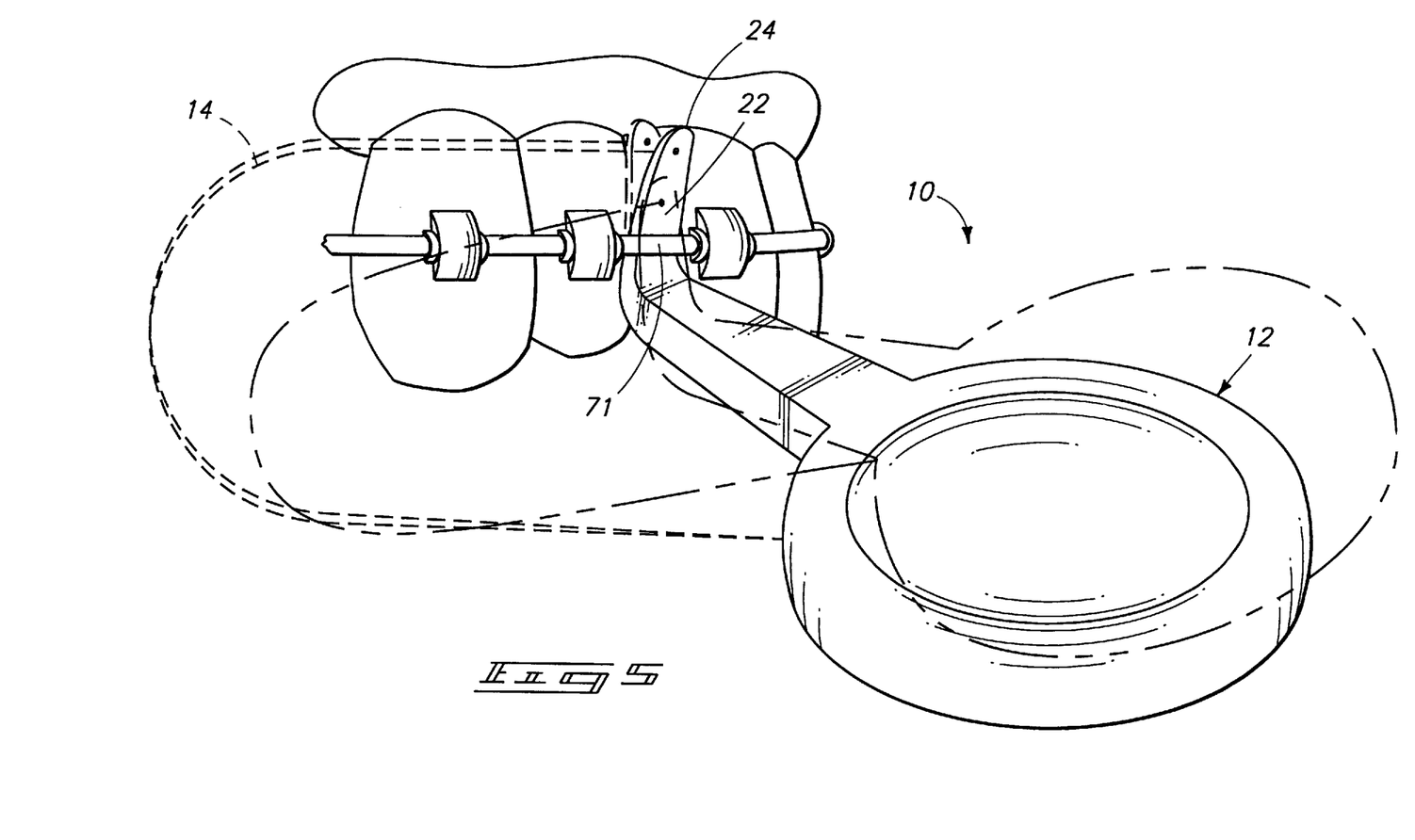
FIG. 5 is a perspective view of the device of FIG. 1 shown in solid lines. The device is shown in operation within a user's mouth.

FIG. 5 shows the flossing device 10 of FIG. 1 in use. In operation, the above-described embodiments provide a dental flossing and dental floss support device which is easy to use, and which enables an individual, particularly those who wear dental braces, to more conveniently and more completely floss between adjacent teeth. In the case of brace wearers, this can be done despite the impedance associated with a brace wire spanning the user's teeth. As a first aspect the methods include selecting a flossing device having suitable features, such as one or more of the features of flossing devices 10, 11, 34 and 100.

In FIG. 2 flosser 10 is shown held in a user's hand in an engaged position after gripping by the user. The user performs the gripping action upon a suitable flossing device selected by the user, such as one having any one or all of the features individually or conjunctively as described above.

FIG. 5 shows flosser 10 in an installed operative position as used with a brace wearer and in position relative to teeth being flossed. In use, an individual wishing to floss their teeth has grasped grip 12, such as between a thumb and forefinger. Thereafter the brace wearing user performs by inserting an insertable portion of the extension between a brace wire and the user's tooth or teeth. The floss-supporting extension 22, even more specifically distal end 24 thereof, is inserted into a working space between a brace spanning wire 71 and adjacent teeth. Associated with this inserting function, is an action involving installing the strand of floss in the intersticial space between the adjacent teeth. This installing action positions the attached floss loop 14 with a segment in the intersticial space in preparation for cleaning the gums and between the adjacent teeth.

The extension 22 allows the attachment point of the floss loop to be positioned sufficiently close to the gum line so as to bring the active region of the floss loop into position within the interstice of the teeth for various movements. More particularly, the active region of the floss loop can be reciprocated longitudinally to help remove tooth and gum line deposits. The active region of the floss loop can also be moved up and down and rocked in a rocking motion (as depicted in FIG. 5). These actions alone or together cause the floss strand to bear along the adjacent edges of the teeth to further remove tooth deposits. These and most other additional aspects of the flossing action and methods described below will be understood to apply equally to all of the embodiments described above.

To place the device in the operative engaged position, an individual need only slip a distal end, in this case distal end 24, under a brace wire 71 and move extension arm part 22 to the position shown in solid lines. This may involve angling the flossing device in a direction which facilitates start of the insertable portion parallel to the face of the teeth, followed by insertion and re-angling to maintain the parallel relationship as the extension is fed into the working space between brace wire and tooth.

The intersticial positioning of the strand of floss, typically also includes concurrent positioning of part of the loop of floss 14 within the lingual side of the teeth with engagement by an individual's finger so that the floss may be tensioned and inserted into a space between adjacent teeth. The user's opposing index finger will generally be most convenient and effective for grasping the medial or lingual curve of the loop. Such finger supports the loop on the medial side of the teeth, whereas the grip 12 and tension 22 will remain on the distal side of the teeth.

After the floss is so inserted, complete flossing action is possible because the device may be moved for carrying the floss to different locations relative to the adjacent teeth, to the brace spanning wire. Such moving action causes the strand of floss to move relative to the teeth and gums to dislodge materials therefrom. One such movement is suggested as shown in lines in FIG. 5 where the double dashed lines depict grip 12 moved upwardly and downwardly to adjust the penetration of the distal end of extension 22, or to performing a rocking action which adjusts the relative pitch of the device. Adjustment of the pitch can allow relative longitudinal reciprocal movement of the floss in the intersticial space between the teeth.

Grip 12 and the attached extension 22 can also be moved by rolling angularly from side-to-side to adjust the interaction with the teeth thus changing the roll orientation. Grip 12 can further be rolled about the axis 23 to facilitate achieving desired positions and levels of force engagement with the adjacent teeth. Moving the device can also be done so as to perform a yawing action which tends to reach different contact points along the faces of the affected teeth. The yawing action pivots about a vertical axis.

The dashed line depiction of extension arm part 22 further shows that the arm part is preferably flexible in response to finger-developed tension on the floss loop which promotes the longitudinal reciprocal action by the active region of the floss strand.

The embodiment of FIG. 4, in addition to providing the above-discussed advantages, also provides a user with a supply of floss which allows the apparatus to be used multiple times without refill. The multi-stand supply flosser is used in a manner similar to the other embodiments except with regard to its preparation for use and replacement of the previously-used floss loop with a fresh strand of floss. This is accomplished by grasping the segment of floss extending from the tie-off 64 and disconnecting the floss. The user then pulls upon the floss strand and cause floss to be dispensed from the spool 48. When a sufficient amount has been dispensed to provide part or all of loop 44 with clean and unworn floss, then the strand is again secured about the tie-off 64.

It is also noteworthy that use of the third embodiment flosser 34 is further performed by gripping the precursor floss segment which extends across the floss exposure area 50. This is advantageously done by pressing the user's finger into the recess 52, thus bearing down on or pinching this segment of the floss to the frame. The opposing strand segments of the floss loop 44 are secured by the tie-off 64, or other suitable means.

The invention further includes additional aspects which can be parts of the preferred methods. The methods relate most generally to flossing, and in greater particularity to flossing teeth which are fitted with corrective dental braces. In one aspect the novel methods can include forming a loop of dental floss affixed or otherwise supported upon a flossing device. The flossing device supports and allows insertion of the floss, particularly in and around dental brace wires. The forming step includes supporting opposing portions of a strand of floss which is to be formed into the floss loop. The supporting can be done by securing points of the floss to floss support features. This supporting can be done in either a detachable temporary manner, or in a relatively more permanent or permanent manner as is described above in connection with the first and second embodiments, and one or more of the connection features used.

The loop forming step can additionally be performed in connection with the third embodiment by releasing one portion of the floss strand from the second floss loop connection feature 64 and then pulling upon the floss. This effects a dispensing of the dental floss from a floss supply mounted upon the flosser frame. The loop forming in such embodiment then further includes tying or otherwise securing the strand of floss, such as at tie-off 64.

The third embodiment can also be used to effect a cutting action of the displaced portion of the floss strand, such as by pulling the displaced strand against cutter 66 to perform this action. This is typically followed by removing the cut displaced portion of floss, and disposing of such in a suitable location.

The novel methods can in some embodiments further include supporting a medial portion of the floss loop upon the user's finger along medial or lingual surfaces of the user's teeth. This supporting is in complementary relationship to the grasping which occurs at the frame, such as frame 36 or grip 12. This provides a operational condition in which the floss loop and connected support device which form the flosser are held between the user's hands or are otherwise held to perform a displacing between the medial portion of the floss loop and the grip. This displacing also effects a tensioning of the active or both segments of the floss loop 44.

With the flosser installed in the proper intersticial position, the user can then perform the desired flossing actions. The flosser can be manipulated to change height, pitch, yaw, roll and performing reciprocating actions. The person's finger which supports the floss loop directly on the medial side of the teeth can additionally be manipulated to effect the reciprocating longitudinal action in the active strand portion of the floss loop. Flexibility in the arm of the flosser, particularly extension part of the arm can allow the user to obtain the desired reciprocal action without necessarily having to move the frame of the flosser. Thus the distal portions of the extension arm in particular can be forced into a bending action using the strength of the finger positioned upon the medial side of the teeth.

After the flossing has been completed the user typically performs an extracting step during which the active strand of the floss loop is removed by pulling it from the intersticial position. The extracting step also typically includes a removing or withdrawing of the arm from between the brace wire and distal surfaces of the teeth.

The embodiment of FIGS. 6–12 also has additional aspects associated with the preferred methods. As explained above, the user typically also employs a forcing action which tends to force a more flexible extension, such as first extension 141 against the teeth. This forcing causes a counteractive bending or flexing of the more flexible, first extension 141. The greater bending is compared to or relative to the associated bending experienced by the relatively less flexible other or second extension 142. This causes a tensioning of the strand 150 which improves control and utility of the strand when performing the moving actions. The moving actions are such as described above in connection with the other embodiments, but which also apply totally or to a large extent to use of flosser 100.

In addition to the forcing and associated flexing of the first extension 141. There is also action associated with the interaction between the curved face 165 and the user's tooth or teeth. The curved face 165 is also advantageously subjected to a forcing action which forces the curved face against the teeth. This leads to the bending and flexing described above and in a similar fashion. The curved surface also allows a rocking action to occur when the user performs a pitching motion with the grip and attached arm 120. The rocking action can be associated with limited rolling engagement between the curved face 165 and user's teeth, or there can be combined rolling and sliding action relative to the teeth.

Manner of Making

The embodiments described herein may be made from a variety of suitable material ranging from injection-molded plastic to stainless steel, and other materials. One preferred material is nylon. Other plastics, such as polycarbonate and others are also believed to be equally suitable and considered preferred materials of construction. The chosen materials are formed in any appropriate manner into the structures described herein. One preferred method of construction is to mold the devices in a single molding operation which would also involve at the same time molding the dental floss strand into any extension or extensions to which the floss is to be permanently affixed. Any undesired excess floss can then be trimmed and the product readied for use by cleaning. It is contemplated that the devices would be for singular or a limited number of uses, such as 1–10 uses, after which the articles would be disposable.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A dental flossing device, comprising:
   a grip;
   a main arm connected to the grip and extending therefrom;
   a first extension connected to the main arm proximate to said grip and having a distal end, said first extension also having a floss support feature formed near the distal end; the first extension having a slender shape which allows the first extension to be inserted between a user's teeth and a brace wire; said first extension further having a curved inward face which can be pressed against a user's teeth;
   a second extension connected to the main arm outward of said first extension and having a distal end, said second extension also having a floss support feature formed near the distal end;
   a strand of dental floss supported between said first and second extensions, said strand of dental floss being support by the first and second extensions at said floss support features;
   wherein said first extension is relatively more flexible in bending as compared to the second extension to allow a user to tension the strand of dental floss by forcing the first extension against surfaces of the user's teeth to thereby bend the more flexible extension relative to the other of said extensions and tension the strand of dental floss.

2. A dental flossing device according to claim 1 wherein the first extension is curved convexly along the inward face.

3. A dental flossing device according to claim 1 wherein the first and second extensions extend away from the main arm at an angle in the range of between approximately 45 to 135 degrees of arc.

4. A dental flossing device according to claim 1 wherein the grip includes a flattened handle that facilitates applying torque by a user about a main arm axis.

5. A dental flossing device according to claim 1 and further defined by
   said main arm having a main arm offset;
   whereby the grip and offset of the main arm act as a supporting rest for the dental flossing device when laid upon a flat surface.

6. A dental flossing device according to claim 1 wherein the grip is a planar member.

7. A dental flossing device according to claim 1 wherein the grip is a planar member oriented approximately orthogonal to an offset axis defined by said main arm offset.

8. A dental flossing device according to claim 1 wherein the grip is a triangular planar member.

9. A dental flossing device according to claim 1 wherein the grip is a triangular planar member oriented approximately orthogonal to an offset axis defined by said main arm offset.

10. A method for flossing teeth, comprising:
    gripping a dental flossing device having a grip, a main arm, a first extension connected to the main arm proximate to the grip, and a second extension connected to the main arm outward of the first arm; the dental flossing device further having a strand of dental floss supported between distal ends of the first and second extensions; the first extension being slender to allow insertion of the first extension between a brace wire and teeth of a user; the first extension also being more flexible in bending than the second extension;

inserting the first extension between a brace wire and teeth of a user;

forcing the first extension against surfaces of the user's teeth to thereby bend the first extension relative to the second extension to tension the strand of dental floss;

moving said strand of dental floss relative to the tooth and adjacent gums to dislodge materials therefrom.

11. A method according to claim 10 wherein;

the first extension includes a curved inward surface which is along an interior face which engages teeth of a user;

the moving step includes rocking the dental flossing device against teeth of the user.

* * * * *